United States Patent [19]

Hong et al.

[11] Patent Number: 5,585,399
[45] Date of Patent: Dec. 17, 1996

[54] METHOD OF PROTECTING CELLS AND TISSUES BY A TRIACYLGLYCEROL PREPARATION

[76] Inventors: Chuang-Ye Hong, 5th Floor, 308, Shi-Pai Road, Sec. 2; Li-Ju Lai, 2F, No. 6, Alley 26, Lane 174 Tung-Hwa Street, Peitou; Sheau-Farn Yeh, #201, Shi-Pai Road, Sec. 2, E174-3, all of Taipei, Taiwan

[21] Appl. No.: 183,538

[22] Filed: Jan. 18, 1994

[51] Int. Cl.$^6$ .................. A61K 31/22; A61K 31/205; A61K 31/20; A61K 47/00
[52] U.S. Cl. .................. 514/546; 514/556; 514/558; 514/560; 514/783; 514/814; 514/815
[58] Field of Search .................. 514/556, 558, 514/560, 814, 815, 783, 546

[56] References Cited

PUBLICATIONS

*The Merck Index*, Tenth Edition, Windholz et al. 1983 p. No. 790; abstract No. 5332.

"Linoleate–Rich Triacylglycerol in Panax pseudo–ginseng Improves Erythrocyte Deformability in vitro"; C. Y. Hong, L. J. Lai, and S. F. Yeh; Jornal of Medicinal Plant Research, vol. 59, Aug. '93, p. 323.

"Effect of Triacylglycerols, on Erythrocyte Deformability In Vitro"; C. Y. Hong, L. J. Lai, M. S. Shiao, and B. N. Chiang; Prostaglandins, Leukotrienes and Essential Fatty Acids, vol. 48, No. 5, May '93, p. 351.

*Primary Examiner*—Kevin E. Weddington
*Attorney, Agent, or Firm*—Curtis, Morris & Safford, PC

[57] ABSTRACT

The present invention relates to a method of using a preparation of triacylglycerol which contains unsaturated fatty acids having no more than two double bonds to preserve normal erythrocyte deformability, to improve microcirculation, to protect myocardium against ischemic damage and to suppress arrhythmia in ischemic heart, i.e. to protect cells and tissues of a mammalian body against various forms of mechanical and chemical injuries.

18 Claims, 2 Drawing Sheets

METHOD OF PROTECTING CELLS AND TISSUES BY A TRIACYLGLYCEROL PREPARATION

FIELD OF THE INVENTION

The present invention relates to a method of using a preparation of triacylglycerol for the protection of cells and tissues of a mammalian body and more particularly, relates to a method of using a preparation of triacylglycerol which contains unsaturated fatty acids, at least one of such fatty acids having no more than two double bonds to prevent injury to cells and tissues of a mammalian body.

BACKGROUND OF THE INVENTION

Reduced deformability of red blood cells (RBC, also known as erythrocyte), is a type of cellular injury. It has been identified as one of the causes of abnormal microcirculation. Several diseases, such as sickle cell anemia, diabetes mellitus and stroke, are also associated with impaired RBC deformability. It is known that ATP depletion or the flexibility of erythrocyte membranes can be reduced by calcium load. Besides, modification of lipid properties may also affect RBC deformability since the erythrocyte membrane includes a lipid bilayer.

Triacylglycerols (TG) are important constituents of blood. 1.7 m M/liter TG are normally present in the plasma of a healthy adult. Since TG are hydrophobic in nature, most of them are bound to lipoproteins when they are circulating in the bloodstream. They are hydrolyzed by lipase and the released free fatty acids are transported into the tissues. Lipid storage has been recognized as the main physiological function of TG. Few studies have been undertaken to investigate if TG has other biological activities. No one has previously evaluated the therapeutic application of a solution of TG as a pharmaceutical preparation which is either mixed with cells or injected into a mammalian body.

There are various kinds of fatty acids contained in triacylglycerols. For a naturally occuring TG, it is very rare to find the same fatty acid component in all three ester positions. In other words, nearly all naturally occuring TG are mixed TG.

Fatty acids are straight chain hydrocarbons that are either saturated or unsaturated. Unsaturated fatty acids contain double bonds while the saturated ones do not. Based on the degree of saturation, unsaturated fatty acids can be either monounsaturated or polyunsaturated. It is known that the fatty acid component contained in the lipids may influence the physical property as well as the biological activity of the lipids. For instance, in an article by M. F. Oliver "cigarette smoking, polyunsaturated fats, linoleic acid, and coronary heart disease" Lancet, 1989 Vol. 333, 1241, it was concluded that people with high risk of coronary artery disease should take more polyunsaturated fatty acids and particularly, those rich in linoleic acid. Another recent study, Lepran, et al., Journal of Cardiovascular Pharmacology 1992, Vol. 19, 40, showed that in rats fed with linoleic acid-rich diet, the occurrence of life-threatening arrhythmia was decreased both during the acute phase of myocardial ischemia and during the reperfusion. However, even though these studies claimed a beneficial effect of oleic acid-rich or linoleic acid-rich diet, the therapeutic application of a preparation containing triacylglycerols with fatty acids of either oleic acid or linoleic acid or others as the only type of esterified acid component has not been disclosed.

Reduced erythrocyte deformability is implicated in the pathogenesis of abnormal microcirculation of blood. It has also been reported that RBC deformability is reduced in patients undergoing cardiopulmonary bypass. Obstruction of microcirculation may cause tissue damage, such as ischemia and the infraction of brain, heart and kidney. These damages may lead to organ dysfunction and increase the morbidity as well as the mortality of the patients.

Presently, several other drugs such as pentoxyfylline, vinpocetin and piracetam are proposed for use in improving RBC deformability. However, these drugs are not suitable for cardiac patients undergoing cardiopulmonary bypass because they have other pharmacological activities and possible adverse effects on the cardiovascular system.

It is therefore an object of the present invention to provide a method of preserving RBC deformability of a mammalian body by using a pharmaceutical preparation.

It is another object of the present invention to provide a method of preserving and improving RBC deformability of a mammalian body by using a pharmaceutical preparation which does not have adverse pharmacological activities on the cardiovascular system.

It is a further object of the present invention to provide a method of improving RBC deformability of a mammalian body by using a pharmaceutical preparation which contains a substance that is normally found in the bloodstream of such mammalian body.

It is yet another object of the present invention to provide a method of preventing injury to cells and tissues of a mammalian body by treating such cells and tissues with a pharmaceutical preparation that does not adversely influence cardiovascular functions of the mammalian body.

It is still another object of the present invention to provide a method of preventing injury to cells and tissues of a mammalian body by introducing into the bloodstream of said body a pharmaceutical preparation that contains triacylglycerol in a pharmaceutically effective amount.

SUMMARY OF THE INVENTION

In accordance with the present invention, a method of preserving RBC deformability and preventing injury to cells and tissues of a mammalian body by using a pharmaceutical preparation containing triacylglycerol is provided.

In the preferred embodiment, the method is provided by using a pharmaceutical preparation of a solution of triacylglycerol which contains unsaturated fatty acids with no more than two double bonds. This preparation can be used either in contact with cells and tissues or it can be injected into the bloodstream of a mammalian body. The preparation was found to preserve normal erythrocyte deformability, to improve microcirculation, to protect myocardium against ischemic damage and to suppress arrhythmia in an ischemic heart. The pharmaceutical preparation can therefore be used to protect cells and tissues against various forms of mechanical and chemical injury.

The most effective pharmaceutical preparations according to the present invention are solutions of tripalmitolein, triolein, trilinolein or mixtures thereof which are triglycerols containing fatty acids having one or two double bonds. Suitable concentrations of these triglycerols in a pharmaceutical preparation to improve RBC deformability were found to be in the range of $10^{-11}$ mole/liter to $10^{-7}$ mole/liter when applied to cells or tissues. Suitable concentrations for injection of the pharmaceutical preparations into the bloodstream of a mammalian body is between $10^{-11}$ to $10^{-9}$ gm/kg of the body weight.

The present invention is further directed to a pharmaceutical preparation of triacylglycerol that contains unsaturated fatty acids having no more than two double bonds. The triacylglycerol is either a tripalmitolein, triolein or trilinolein, or mixtures thereof. The preparation can be used in an amount that is pharmaceutically effective either in a solution exposed to cells or tissues or in a solution injected into the bloodstream of a mammalian body.

BRIEF DESCRIPTION OF THE DRAWINGS

Other objects, features and advantages of the present invention will become apparent upon consideration of the specification and the appended drawings, in which.

DETAILED DESCRIPTION OF THE PREFERRED EMBODIMENT

Figure 1:
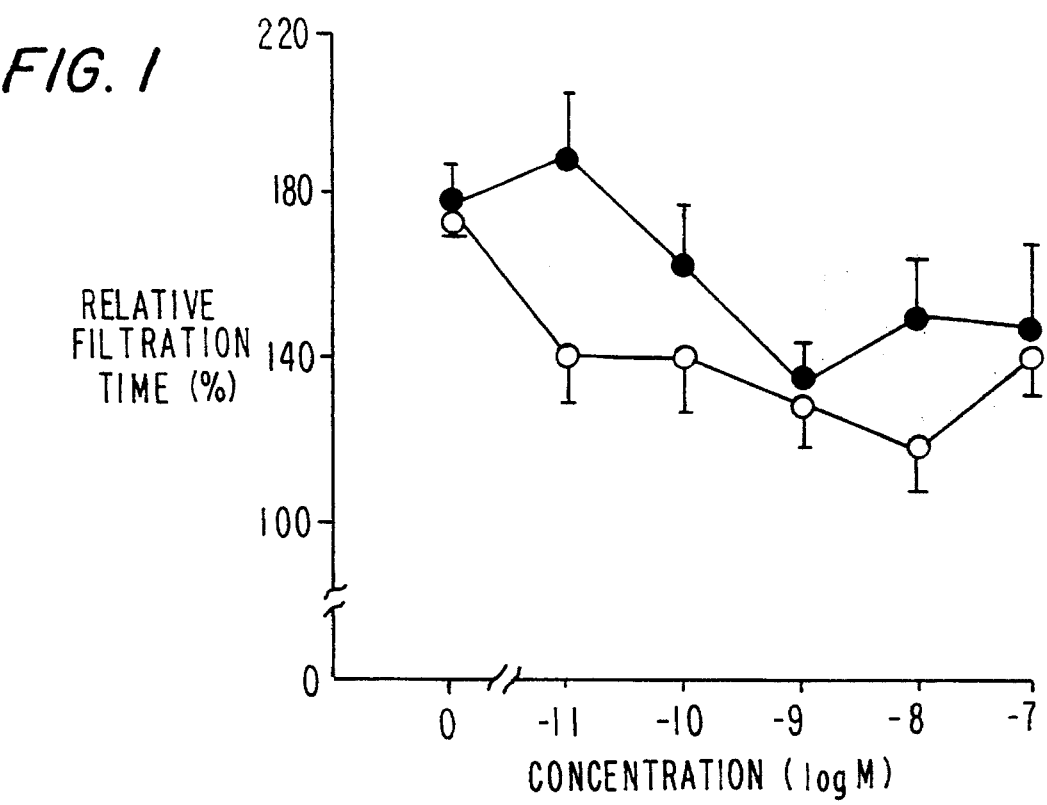
FIG. 1 is a graph showing the effect of trilinolein and the active component of Panax pseudo-ginseng on erythrocyte deformability.

The present invention discloses a method of preserving and improving RBC deformability by using a pharmaceutical preparation of triacylglycerol which contains unsaturated fatty acids having no more than two double bonds.

In an attempt to investigate the physiological effect of traditional Chinese medicinal herbs on various diseases related to the heart, a number of herbs were tested and it was accidentally discovered that one of these Chinese herbs, Panax pseudo-ginseng produces an extract that has beneficial effect on preserving RBC deformability.

Root of Panax pseudo-ginseng Wall. var. notoginseng (Burk.) (PP), also known as Sanchi, is a herbal drug widely used in traditional Chinese medicine for the treatment of cardiovascular diseases. Although well designed, controlled trials have yet to be undertaken to evaluate its clinical efficacy. Recently, its total saponins were demonstrated to inhibit the norepinephrine-induced arterial contraction and a blocking effect on receptor-operated calcium channel was proposed as a pharmacological mechanism for its saponin fraction. No one has previously reported any experiments on the purification and identification from PP of an active component that improves RBC deformability in vitro.

Extraction of Panax Pseudo-Ginseng

Dried roots of PP were purchased from a local market. They were pulverized and extracted with n-hexane. After evaporation of the solvent, the concentrated extract was chromatographed over a silica gel column and eluted with n-hexane and ethylacetate (EtOAc) mixtures of increasing polarity. The collected fractions were monitored with thin layer chromatography (TLC) in a solvent system containing 90% n-hexane and 10% EtOAc. The fractions which improved RBC deformability were subjected to repeated column chromatography and finally purified with preparative TLC on silica gel precoated plates (Nerck, Germany). For RBC deformability assay, a small volume of PP extract was dissolved in DMSO and then diluted in Dulbecco's modified Eagle medium (D-MEM, Flow Laboratories, USA) containing 0.25% w/v bovine albumin (Sigma, USA).

RBC Preparation

Blood samples were collected from healthy volunteers. RBCs were separated from heparinished venous blood by centrifugation at 2000 g for 5 min (Sorvall RT6000B, Du Pont, USA). The bully coat was removed and RBCs were washed twice with 0.9% NaCl solution. Packed RBCs were then mixed with an equal volume of diluted PP extract and incubated at 37° C. (water bath) for 2 h. Except in experiments which studied the interaction between PP and calcium ion, final concentrations of DMSO and calcium ion in the RBC-PP mixture were 0.5% and 10 mM, respectively. At this concentration, DMSO showed no significant effect on RBC deformability. RBC incubated in calcium-free medium (Joklik's minimum essential medium, J-MEM, Gibco Laboratories, USA) containing 0.5% DMSO and 0.25% bovine albumin was used as a control.

RBC Deformability

RBC deformability was tested with a Reid's filtration technique. 5 minutes prior to the test, RBC-PP mixture was diluted ten folds with a J-MEM. 1.5 ml of diluted RBC-PP mixture in a disposable syringe was made to flow through the 5 micron pores of a 13 mm diameter polycarbonate membrane filter (Nuclepore Corporation, Pleasanton, Calif., USA) by applying 5 cm $H_2O$ negative pressure in a recipient bottle. Relative filtration time is the ratio of filtration time for RBC-PP mixture incubated in calcium containing D-MEM to the filtration time for RBC incubated in calcium-free J-MEM.

Authentic Lipids

Glycerol, linoleic acid, dilinoleoyl phosphatidyl choline, and authentic triacylglycerols including tripalmitin, tripalmitolein, tristearin, triolein, trilinolein, trilinolenin and triarachidonin were purchased from Sigma (USA). They were first dissolved and serially diluted in chloroform. After chloroform was evaporated, they were dissolved in Dulbecco's modified Eagle medium (D-MEM, Flow Laboratories, USA) which contained 20 mM calcium, 0.25% W/V bovine albumin (Sigma, USA) and 1% DMSO.

Identification of Active Compound

Chemical structure of the purified component was determined by spectroscopic methods. Proton and $C^{13}$-NNR were obtained on a Bruker AM-400 MHz NMR spectrometer and reported as parts per million downfield from $Me_4Si$ ($\delta$=0). Mass spectra were recorded using a Jeol JMS-HX 110 mass spectrometer and are reported as m/z.

Experimental Results

The active component in the n-hexane extract of PP was found to be present in a fraction that can be eluted from silica gel chromatography with 3 to 5% EtOAc in n-hexane. After repeated fractionation by silica gel chromatography with 2 to 6% EtOAc in n-hexane as eluents, an active fraction was applied to a 1 mm thick preparative silica gel TLC plate and a pure compound was obtained.

Structural determination of the active compound was primarily based on NMR and mass spectrometry. Mass spectrum of this compound gave a molecular ion peak at m/z 878 $[C_{57}H_{98}O_6]^+$ and the major fragment ion peaks at m/z 599 $[M-C_{18}H_{31}O_2]^+$. This mass fragmentation pattern strongly suggested that this compound is a triacylglycerol (TG) with linoleic acid as the major fatty acid residue in the esterified positions of glycerol. The proton and broad-band decoupled $C^{13}$-NMR spectra of this active compound were also indicative of a TG with a fatty acid residue with two unsaturated double bonds. From the NNR spectra, it could be estimated that more than 90% of the fatty acids contained in this TG were linoleic acids. Small amounts of oleic acid and linolenic acid may also be present in the TG. The structure of a TG with linoleic acid was confirmed by comparison of the NNR spectra with that of soybean oil which had linoleic acid as the major fatty acid in its TG.

concentration of $10^{-11}$ mole/liter ($p<0.05$, t-test). This is most likely due to the fact that small amounts of oleic acid and linolenic acid were present in the TG obtained from PP.

Figure 2:
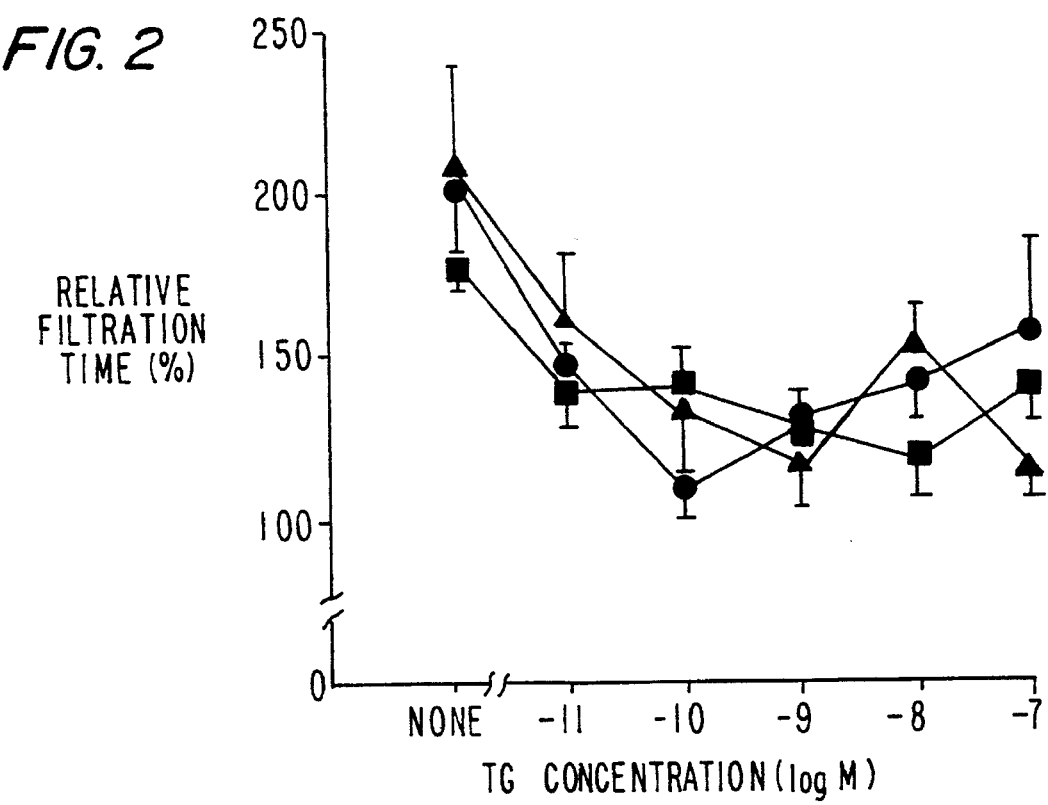
FIG. 2 is a graph showing the dependence of the relative filtration times on the concentrations of the three triacylgycerols of trilinolein, tripalmitolein and triolein.

FIG. 2 shows that in the absence of TG, filtration time for RBC in the calcium-containing medium was increased while trilinolein, tripalmitolein and triolein reversed the relative filtration time towards the control. Table 1 shows the actual data of filtration times and relative filtration time (percent of control) for RBC treated with three TG, namely tripalmitolein, triolein and trilinolein. RBC in a calcium-free medium was used as a control. Data are obtained on six samples. The differences in the effects of these three TG were not statistically significant. It should be noted that at higher concentration ranges, i.e. up to $10^{-5}$ mole/liter, the beneficial effect of TG is still observed.

TABLE 1

| $Ca^{+2}$ | TG (mole/L) | tripalmitolein | triolein | trilinolein |
|---|---|---|---|---|
| − | 0 | 8.27 ± 0.74 (100%) | 8.27 ± 0.74 (100%) | 8.85 ± 0.70 (100%) |
| + | 0 | 16.75 ± 2.35 (207.43 ± 33.21%) | 16.75 ± 2.35 (207.43 ± 33.21%) | 15.70 ± 1.12 (178.34 ± 6.74%) |
| + | $10^{-11}$ | 12.83 ± 1.41 (160.88 ± 22.18%) | 12.23 ± 1.25 (147.84 ± 6.75%) | 12.07 ± 0.36 (140.68 ± 11.68%) |
| + | $10^{-10}$ | 10.65 ± 1.14 (132.66 ± 17.27%) | 9.00 ± 0.85 (110.28 ± 8.57%) | 12.12 ± 0.96 (140.20 ± 13.40%) |
| + | $10^{-9}$ | 9.73 ± 1.19 (117.33 ± 9.17%) | 10.37 ± 0.70 (128.87 ± 11.94%) | 11.27 ± 0.82 (129.29 ± 10.20%) |
| + | $10^{-8}$ | 12.90 ± 1.75 (154.66 ± 11.52%) | 11.62 ± 0.96 (142.19 ± 10.08%) | 10.25 ± 0.70 (118.42 ± 10.59%) |
| + | $10^{-7}$ | 9.35 ± 0.55 (115.46 ± 7.52%) | 12.67 ± 2.01 (158.40 ± 29.40%) | 12.45 ± 1.27 (140.60 ± 9.82%) |

It was also found that glycerol, linoleic acid, dilinoleoyl phosphatidyl choline, tripalmitin, tristearin, trilinolein and triarachidonin had no statistically significant effect on RBC deformability. These data are shown in Table 2 of relative filtration time (percent of control) for RBC treated with various kinds of lipids. RBC in a calcium-free medium was used as a control while data are obtained on six samples.

TABLE 2

| $Ca^{+2}$ | lipid (mole/L) | glycerol | linoleic acid | dilinoleoyl phosphatidyl choline | tripalmitin | tristearin | trilinolenin | triarachidonin |
|---|---|---|---|---|---|---|---|---|
| − | 0 | 100 | 100 | 100 | 100 | 100 | 100 | 100 |
| + | 0 | 193.6 ± 17.5 | 178.0 ± 5.3 | 172.8 ± 4.7 | 184.0 ± 5.2 | 183.5 ± 5.6 | 205.0 ± 14.8 | 205.9 ± 14.6 |
| + | $10^{-11}$ | 160.3 ± 16.5 | 142.2 ± 9.9 | 146.6 ± 24.4 | 152.7 ± 13.9 | 196.3 ± 29.8 | 168.1 ± 26.1 | 197.7 ± 24.2 |
| + | $10^{-10}$ | 201.2 ± 24.4 | 156.2 ± 10.9 | 150.7 ± 36.8 | 165.5 ± 23.9 | 186.9 ± 28.6 | 216.6 ± 50.5 | 275.0 ± 38.7 |
| + | $10^{-9}$ | 169.9 ± 16.5 | 148.6 ± 11.0 | 125.7 ± 13.1 | 153.4 ± 20.7 | 238.2 ± 54.8 | 238.7 ± 30.7 | 204.8 ± 24.4 |
| + | $10^{-8}$ | 211.9 ± 40.0 | 228.8 ± 20.4 | 149.5 ± 20.0 | 154.9 ± 10.1 | 189.0 ± 29.4 | 215.2 ± 39.8 | 189.8 ± 25.5 |
| + | $10^{-7}$ | 163.3 ± 23.0 | 228.3 ± 61.5 | 172.0 ± 24.4 | 147.3 ± 13.7 | 148.2 ± 22.5 | 179.9 ± 13.5 | 244.9 ± 33.1 |

FIG. 1 shows that both the active component of PP and authentic trilinolein reduced the relative filtration time. The relative filtration time for RBC in the PP-free, calcium-containing medium (D-MEM) was 176.8±9.6% while the active component of PP at $10^{-9}$ mole/liter reduced the relative filtration time to 134.1±8.2% (mean±standard error of mean, n=7). Authentic trilinolein at $10^{-11}$ mole/liter reduced the relative filtration time to 140.7±11.7% (mean±standard error of mean, n=6). Trilinolein was more potent than the active component of PP ($p<0.05$, analysis of variance) and the difference was statistically significant at a A number of lipids were dissolved in a buffer solution containing DMSO. Packed RBC were prepared by centrifugation of human venous blood. RBC were mixed with the lipid solution and incubated at 37° C. in a water bath for 2 hours. Final concentration of DMSO in the RBC-lipid mixture was 0.5%. At this concentration, DMSO showed no significant effect on RBC deformability. RBC deformability was tested with a filtration method in which the time required for RBC to flow through the 5 micron pores of a polycarbonate membrane filter was measured. Prolongation of the filtration time was used to represent a decrease in RBC deformability. RBC incubated in the calcium-free buffer was used as a control and its filtration time was considered as 100%. Addition of calcium ion to the buffer impaired RBC deformability and prolonged the filtration time.

FIG. 2 shows that trilinolein (■), tripalmitolein (▲) and triolein (●) reduced prolongation of filtration time, thus, increased RBC deformity. Filtration time for RBC in the calcium-free buffer was used as a control (100%). Filtration time in the calcium-containing but TG-free medium was increased to 180–200% of control. In the presence of TG, the filtration time was decreased toward the control. The differences among these three TG were not statistically significant.

Figure 3:
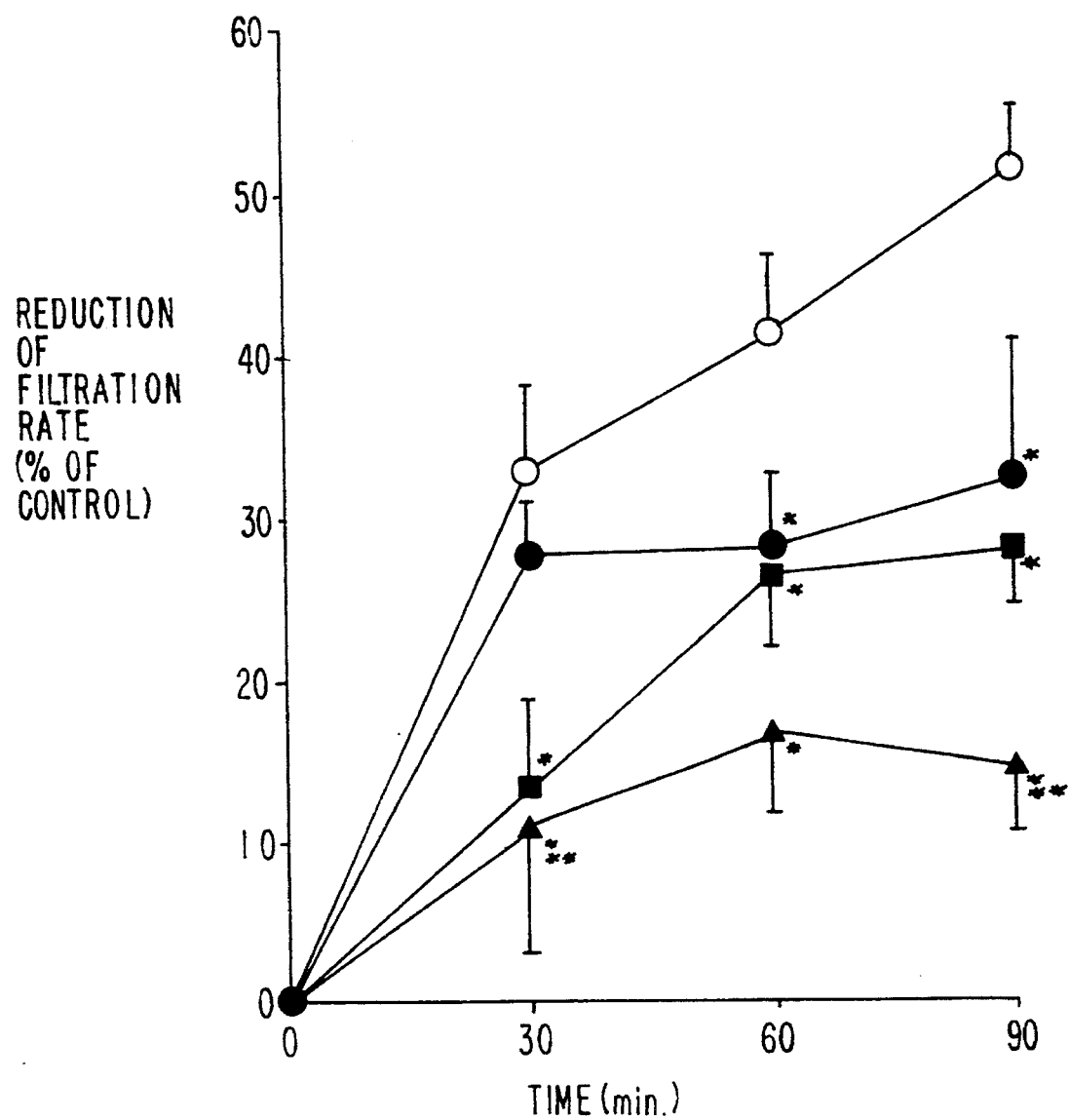
FIG. 3 is a graph showing the reduction in filtration rates as a dependence of time in blood samples collected after a cardiopulmonary bypass-induced reduction in RBC deformability.

FIG. 3 shows that trilinolein reversed the cardiopulmonary bypass (CPB)-induced reduction in RBC deformability as expressed as a reduction in filtration rate. Filtration rate of RBC in blood sample collected before CPB was used as a control (100%). Blood samples collected 30, 60 and 90 minutes after the start of CPB were mixed with either trilinolein-free buffer (0) or $10^{-9}$ mole/liter(●), $10^{-8}$ mole/liter(■) and $10^{-7}$ mole/liter(▲) trilinolein before filtration rate was measured.

Among the lipids tested, only tripalmitolein, triolein and trilinolein improved the deformability of calcium-loaded RBC (see Tables 1, 2 and FIG. 2). These three TG contain palmitoleic acid (16:1), oleic acid (18:1) and linoleic acid (18:2) as the esterified fatty acid respectively. Because glycerol and linoleic acid did not improve RBC deformability, it is unlikely that these TG were hydrolyzed by lipase and then acted on RBC through the released glycerol or fatty acid. In addition, we found that tripalmitin, tristearin, trilinolenin and triarachidonin did not improve RBC deformability. Since these four TG contain palmitic acid (16:0), stearic acid (18:0), linolenic acid (18:3) and arachidonic acid (20:4) respectively, it suggests that activity for TG to improve RBC deformability is specific to those TG which have esterified fatty acids with one or two double bonds.

TG did not improve RBC deformability by acting as a specific antagonist of calcium ion because it was found that at higher calcium concentration, trilinolein only partially reduced the RBC filtration time. In other words, the dose response curves for trilinolein to antagonize the detrimental effect of calcium ion on RBC deformability were not parallel. Although the mechanism responsible for the observed protective effect of these TG has not been elucidated, it is believed that these TG improve RBC deformability by increasing RBC membrane fluidity. Membrane fluidity is one of the major factors in determining RBC deformability. TG are hydrophobic in nature; they could be bound to RBC membrane and change membrane fluidity. Since the degree of fatty acid saturation is closely related to the physical properties of TG, only those TG which contain fatty acids with one or two double bonds could modify RBC membrane fluidity and improve its deformability.

The effective concentrations of tripalmitolein, triolein and trilinolein to improve RBC deformability were in the range between $10^{-11}$ mole/liter to $10^{-5}$ mole/liter, preferably in the range between about $10^{-10}$ mole/liter to about $10^{-6}$ mole/liter and more preferably between about $10^{-9}$ mole/liter to about $10^{-7}$ mole/liter. The differences among the potential of these three TG on RBC deformability are not statistically significant. This effective concentration range is much lower than $1.7 \times 10^{-3}$ mole/liter, which is the normal concentration for lipoprotein-bound TG in the plasma of a healthy human. Even if a low concentration of free TG could be present in serum, it is unlikely that such a free TG in serum is trilinolein, triolein or tripalmitolein since nearly all naturally occurring TG in human body is mixed TG containing at least one saturated fatty acid.

EXAMPLE 1

To prove that TG solution is effective in clinical situations, RBC deformability in blood samples collected from 12 patients who received elective open-heart surgery for coronary bypass graft is studied. Venous blood samples were collected prior to, and 30, 60, 90 minutes after the start of cardiopulmonary bypass. They were first mixed with trilinolein-containing buffer, then centrifuged for preparation of packed RBC. RBC deformability was measured with the aforementioned filtration method. Deformability of RBC in venous blood that had not been mixed with trilinolein was used as a control. As shown in FIG. 3, filtration time was prolonged by cardiopulmonary bypass. This reduction of RBC deformability can be reversed by trilinolein. $10^{-7}$ mole/liter trilinolein was more potent than $10^{-9}$ mole/liter in this effect. Currently, there are several drugs such as pentoxyfylline, vinpocetin and piracetam available to improve RBC deformability. However, they are not suitable for cardiac patients undergoing cardiopulmonary bypass because they all have other pharmacological activities on cardiovascular system. TG, on the other hand, is less likely to influence cardiovascular functions because they are normally present in human body.

EXAMPLE 2

A coronary ligated rat model was used to study the protective effect of TG on myocardium. Male 200–350 gm Sprague-Dawley rats were anestheized with urethane, artificially ventilated through tracheal cannulation with a Harvard rodent ventilator. The chest was opened in the fourth intercostal space and heart exposed. A loop of 6-0 atraumatic silk was placed around the left main coronary artery, approximately 2 mm from its origin. Both ends of the ligature were led out of the thoracic cavity through a flexible tubing. After stabilization of the blood pressure and heart rate (approximately 10 minutes), the loose ligation was tightened and fixed by clamping on the silk and thus local ischemia was produced. Successful induction of ischemia was evidenced by an immediate increase of R wave amplitude form approximately 0.5 mV to over 2 mV on ECG. After 30 minutes of coronary ischemia, the ligature was released and reperfusion was started.

A trilinolein solution for injection was prepared by dissolving trilinolein in 40% propylene glycol in normal saline. This solution was injected into the internal jugular vein through a polyethylene catheter 15 minutes prior to the ligation of coronary artery. Three doses ($10^{-9}$, $10^{-10}$ and $10^{-11}$ gm/kg) were tested, each dose was tested on seven rats. Rats injected with normal saline were used as a control. Carotid artery was cannulated for the measurement of blood pressure. Standard electrocardiogram (lead II, ECG) was recorded, using subcutaneous needle electrodes. The incidence and duration of arrhythmia were registered both during the 30 minutes occlusion and first 10 minutes of reperfusion. Most reperfusion arrhythmia occurred immediately after release of the ligature.

It was found that trilinolein at $10^{-9}$ gm/kg completely abolished ventricular tachycardia (VT) and ventricular fibrillation (VF), both during ischemia and reperfusion. Table 3 shows that the incidence and duration of both ventricular tachycardia and ventricular fibrillation were reduced during the ischemia and Table 4 shows the reduction of arrhythmia during the reperfusion stage. The data showed that in addition to an improvement of erythrocyte deformability and microcirculation, administration of a solution of triacylglycerol which contains specific type of fatty acid can protect myocardium against ischemic damage and suppress life-threatening arrhythmia in ischemic heart.

TABLE 3

| Group | Incidence of VT (%) | Duration of VT (Sec) | Incidence of VF (%) | Duration of VF (Sec) | Dysrrhythmia Incidence (%) |
|---|---|---|---|---|---|
| Control | 71.4 | 130.4 | 36 | 27.6 | 92.8 |
| $10^{-9}$ gm/kg | 0 | 0 | 0 | 0 | 0 |
| $10^{-10}$ gm/kg | 57 | 98.7 | 29 | 80 | 57 |
| $10^{-11}$ gm/kg | 71.4 | 120.7 | 29 | 123.2 | 86 |

TABLE 4

| Group | Incidence of VT (%) | Duration of VT (Sec) | Incidence of VF (%) | Duration of VF (Sec) | Dysrrhythmia Incidence (%) |
|---|---|---|---|---|---|
| Control | 29 | 36.5 | 14 | 11 | 0 |
| $10^{-9}$ gm/kg | 0 | 0 | 0 | 0 | 0 |
| $10^{-10}$ gm/kg | 43 | 13.4 | 0 | 0 | 29 |
| $10^{-11}$ gm/kg | 43 | 76.1 | 29 | 137.1 | 43 |

While the experimental data proved that triacylglycerol solution protected erythrocyte and myocardium, it is not intended to limit the present invention to these specific applications. Since ischemic injury and membrane damage are common in pathological conditions, the present invention can be applied to other cells and tissues, such as salvation of infarcted limbs or organs, preservation of extirpated tissues for transplantation, propagation of cultured cells in unfavorable growth environment, etc. It should also be noted that even though our experimental data shows that unsaturated fatty acids containing one or two double bonds produce the most optimum results, it is expected that one or two fatty acids in the TG may contain more than two double bonds and produce similarly beneficial results.

While the present invention has been described in an illustrative manner, it should be understood that the terminology used is intended to be in a nature of words of description rather than of limitation.

Furthermore, while the present invention has been described in terms of a preferred embodiment thereof, it is to be appreciated that those skilled in the art will readily apply these teachings to other possible variations of the invention.

The embodiments of the invention in which an exclusive property or privilege is claimed are defined as follows:

1. A method for preventing impairment of red blood cell deformability in a patient in need of such treatment comprising the step of contacting red blood cells of said patient with a preparation containing triacylglycerol in a pharmaceutically effective amount, said triacylglycerol contains unsaturated fatty acid having no more than two double bonds.

2. A method according to claim 1, wherein said unsaturated fatty acid is selected from the group consisting of palmitoleic acid, oleic acid and linoleic acid.

3. A method according to claim 1, wherein said pharmaceutically effective amount is between about $10^{-11}$ mole/liter to about $10^{-5}$ mole/liter.

4. A method according to claim 1, wherein said pharmaceutically effective amount is between about $10^{-10}$ mole/liter to about $10^{-6}$ mole/liter.

5. A method according to claim 1, wherein said pharmaceutically effective amount is between about $10^{-9}$ mole/liter to about $10^{-7}$ mole/liter.

6. A method according to claim 1, wherein said patient is a human.

7. A method as claimed in claim 1 wherein the contacting comprises the step of introducing into the bloodstream of said patient the preparation of triacylglycerol in the pharmaceutically effective amount.

8. A method for preventing injury to cells or tissues of a patient in need of such treatment by preventing impairment of red blood cell deformability, said method comprising contacting the cells or tissues with a pharmaceutical preparation containing triglycerol containing unsaturated fatty acid having no more than two double bonds, in a pharmaceutically effective amount.

9. A method as claimed in claim 8, comprising contacting the cells or tissues with a pharmaceutically effective amount of a solution of tripalmitolein, triolein, trilinolein, or a mixture thereof.

10. A method as claimed in claim 8 wherein the pharmaceutically effective amount is a concentration of between about $10^{-11}$ mole/liter and about $10^{-5}$ mole/liter.

11. A method as claimed in claim 10 wherein the concentration is between $10^{-9}$ mole/liter and $10^{-7}$ mole/liter.

12. A method as claimed in claim 8 wherein the pharmaceutically effective amount is a concentration between $10^{-11}$ and $10^{-9}$ gm/kg of body weight of the patient.

13. A method as claimed in claim 8 wherein the triglycerol has esterified fatty acids.

14. A method as claimed in claim 8 wherein the contacting is ex vivo.

15. A method as claimed in claim 8 wherein the contacting is in vivo.

16. A method for improving microcirculation in a patient in need of such treatment comprising contacting red blood cells of said patient with a preparation containing triacylglycerol in a pharmaceutically effective amount, said triacylglycerol contains unsaturated fatty acid having no more than two double bonds.

17. A method for preventing injury to cells or tissues of a patient in need of such treatment by improving microcirculation in said patient, said method comprising contacting red blood cells of said patient with a preparation containing triacylglycerol in a pharmaceutically effective amount, said triacylglycerol contains unsaturated fatty acid having no more than two double bonds.

18. The method of claim 1 wherein the preparation comprises an extract of Panax pseudo-ginseng.

* * * * *